United States Patent
Shah

(10) Patent No.: US 10,926,042 B2
(45) Date of Patent: Feb. 23, 2021

(54) ANIMAL INJECTION CLIP

(71) Applicant: Jayesh Shah, Shohola, PA (US)

(72) Inventor: Jayesh Shah, Shohola, PA (US)

(*) Notice: Subject to any disclaimer, the term of this patent is extended or adjusted under 35 U.S.C. 154(b) by 399 days.

(21) Appl. No.: 15/197,597

(22) Filed: Jun. 29, 2016

(65) Prior Publication Data
US 2018/0001036 A1    Jan. 4, 2018

(51) Int. Cl.
*A61M 5/32* (2006.01)
*A61D 99/00* (2006.01)
*A61D 7/00* (2006.01)

(52) U.S. Cl.
CPC ............ *A61M 5/3287* (2013.01); *A61D 7/00* (2013.01); *A61D 99/00* (2013.01); *A61M 2250/00* (2013.01)

(58) Field of Classification Search
CPC .............. A61B 17/3403; A61B 90/11; A61B 2017/3409; A61B 2090/0811; A61B 17/1322; A61M 5/3287; A61M 5/427; A61M 2202/09; A61M 25/06; A61M 5/32; A61M 2250/00; A61D 99/00; A61D 7/00
USPC ........ 600/424; 604/116, 117, 239, 264, 272, 604/506, 507
See application file for complete search history.

(56) References Cited

U.S. PATENT DOCUMENTS

| | | | | |
|---|---|---|---|---|
| 4,299,219 A * | 11/1981 | Norris, Jr. | ............. | A61M 5/425 604/115 |
| 4,586,924 A * | 5/1986 | Lanning | ................ | A61M 5/425 128/869 |
| 5,415,647 A * | 5/1995 | Pisarik | .................. | A61M 5/425 604/115 |
| 6,117,146 A * | 9/2000 | Slishman | .............. | A61M 5/425 604/116 |
| 7,824,372 B1 * | 11/2010 | Kurup | ................... | A61F 9/0017 604/116 |
| 8,308,740 B2 * | 11/2012 | Tolley | ................ | A61B 17/3403 604/116 |
| 8,702,654 B2 * | 4/2014 | Agee | .............. | A61B 17/320036 600/183 |
| 8,758,300 B2 * | 6/2014 | Bakhtyari-Nejad-Esfahani | .......... | A61M 5/3287 604/117 |
| 9,222,996 B2 * | 12/2015 | Fujimoto | ............. | G01R 33/286 |
| 2009/0149812 A1 * | 6/2009 | MacAulay | ............ | A61M 5/427 604/117 |
| 2010/0137799 A1 * | 6/2010 | Imai | ...................... | A61M 5/158 604/115 |
| 2011/0308478 A1 * | 12/2011 | Lee | .......................... | A61D 3/00 119/752 |
| 2016/0022277 A1 * | 1/2016 | Eikman | .............. | A61B 17/1322 606/203 |

* cited by examiner

Primary Examiner — Jason E Flick

(57) ABSTRACT

The present invention describes a mouse tail vessel injection device. The device consists of a ring situated on top of a platform, which is attached to a tourniquet, and includes a tool to place the device on and off the tail of the mouse. The ring allows access to the lumen of the tail vessel by providing the appropriate angle and width for the needle gauge. The placement tool contains 3 adjustable prongs which insert into the retainer holes attached to the tourniquet, thus allowing expansion and contraction of the tourniquet to move the device on and off the tail.

6 Claims, 3 Drawing Sheets

ANIMAL INJECTION CLIP

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention lies within the field of laboratory animal injection apparatuses.

2. Background of the Invention

The currently employed method of injecting compounds into the tail vessels of laboratory mice requires the researchers to immobilize the mouse, identify the vessel of choice, and manually puncture it with the needle. The method requires plenty of patience, skill, and steady hands. Nevertheless, researchers still have a very low success rate and injection material and mice are wasted. Many tips and technique variations have been explored, but majority are not universally applicable or still requires experience. Currently, researchers practice injecting tail vessels with saline solution prior to injecting the compound of interest. Again, this wastes mice and time for the research group.

The needle gauge and bore size plays a large factor, as well. Higher gauge needles will be more successful in puncturing the vessels, but if the compound is large, then shearing forces will damage the compound and render it useless. On the other hand, lower gauge needles will not damage the compound, but puncturing the vessels will be difficult. A highly skilled research worker will be able to inject the compound using a lower gauge needle, but the success rate is still not optimal, and practice must still occur prior to the compound injection.

An automated apparatus has been made by Chang et al (US 20140236045 A1) which removes much of the user input and allows for a higher injection success rate. The device utilizes a positioning system, infrared light and cameras, pressure monitoring system, and automated injection. The user simply has to place the animal onto the bed, and set up the machine with the appropriate parameters and the compound. While the system is very useful and provides a great advantage, there are several issues to note. First, as with all machines, a great amount of trust has to be placed in the apparatus to successfully inject the compound and inject the correct amount. Of course, with proper calibration, this issue may be nulled, but calibration takes time and money, and to do so for every time an injection experiment has to take place, the costs will add up. Additionally, if many mice are to be injected during one sitting, then calibrations will have to occur during this run, and the research worker will need to be adept at calibrating the machine. Second, the pressure monitoring system places a pressure transducer within the lumen of the needle. Not only is this a sterility issue, but the internal diameter of the needle is reduced and therefore causes the compounds to succumb to shearing forces. Also, the needle used in the apparatus is not disposable. Therefore, a cross-contamination issue arises. Third, despite all the features available, the system only maintains a modest improvement in accuracy and repeatability over experienced researchers. The cost of such a system would be high, and to only receive a modest improvement would hinder many researchers from purchasing the system.

Phlebotomy is a widely used technique in the medical field. Applying such techniques to mice was inevitable. A common phlebotomy technique is to use a tourniquet to enlarge the vessel of choice to ease injection. Harvey Minasian (1980) devised a simple tourniquet to aid in mouse tail venipuncture. The tourniquet involves the use of a thread, sewing needle, and a syringe. Although the tourniquet is simple and useful in enlarging the vessel, it is unable to allow the researcher to accurately puncture the vessel to the appropriate depth, and requires the user to assemble the tourniquet. Issues arise when the user has to control the tensioning and relaxation of the tourniquet.

An economical system with more user input and ease of access to the vessel would allow for a higher success rate. An experienced researcher will likely be able to feel if the needle is within the vein. Their only need would be to speed the injection process and increase the accuracy. Therefore, an economically disposable apparatus will be of greater use and remove all the disadvantages mentioned earlier.

BRIEF SUMMARY OF THE INVENTION

The present invention will help to address the shortcomings of the previously employed methods of tail vein injection as well as the automated system. The invention mentioned herein employs a commonly used technique applied in phlebotomy, the use of a tourniquet. However, the present invention has an additional ring located attached above the tourniquet. The user places the tourniquet around the tail of the mouse by sliding it over the end of the tail up towards the base until a resistance is felt. The tourniquet is positioned so that the ring lies above the vein of choice. The user then inserts their needle within the bore of the ring. The ring's size and angle will allow the needle to insert enough to puncture the vessel and at the proper angle to successfully inject the compound. Each ring will be tailored to fit a specific needle gauge size and length. This method will place the user in more control of the injection and allow for higher accuracy. In addition, the disposable nature of the ring will prevent sterility and cross-contamination issues. Finally, the low cost of producing the invention will be more economically desirable for researchers.

Variations can be made to the invention, such as the use of an infrared light system to visualize the vein on a screen or light polarizing glass, a marking to signify the direction and size of the needle, color variations to match the respective needles, a tool to place the tourniquet at a position without sliding it along the tail, and a ring that can accommodate more than one needle size.

BRIEF DESCRIPTION OF THE SEVERAL VIEWS OF THE DRAWING

Below are brief descriptions of the included illustrations, including applicable variations.

DETAILED DESCRIPTION OF THE INVENTION

Figure 1:
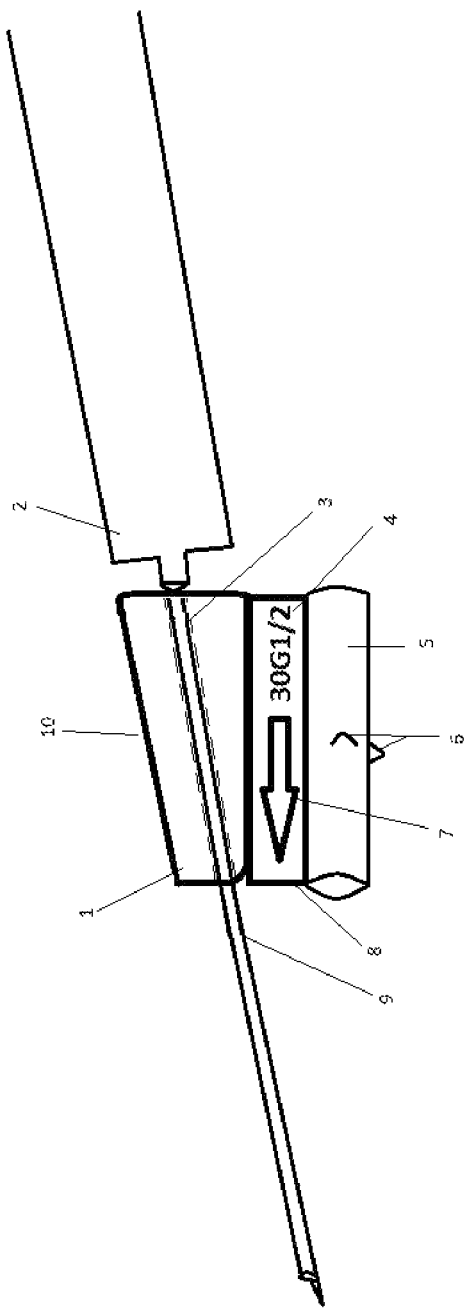
FIG. 1 depicts the tourniquet, the ring's angle and the markings for the needle direction and size.
Figure 2:
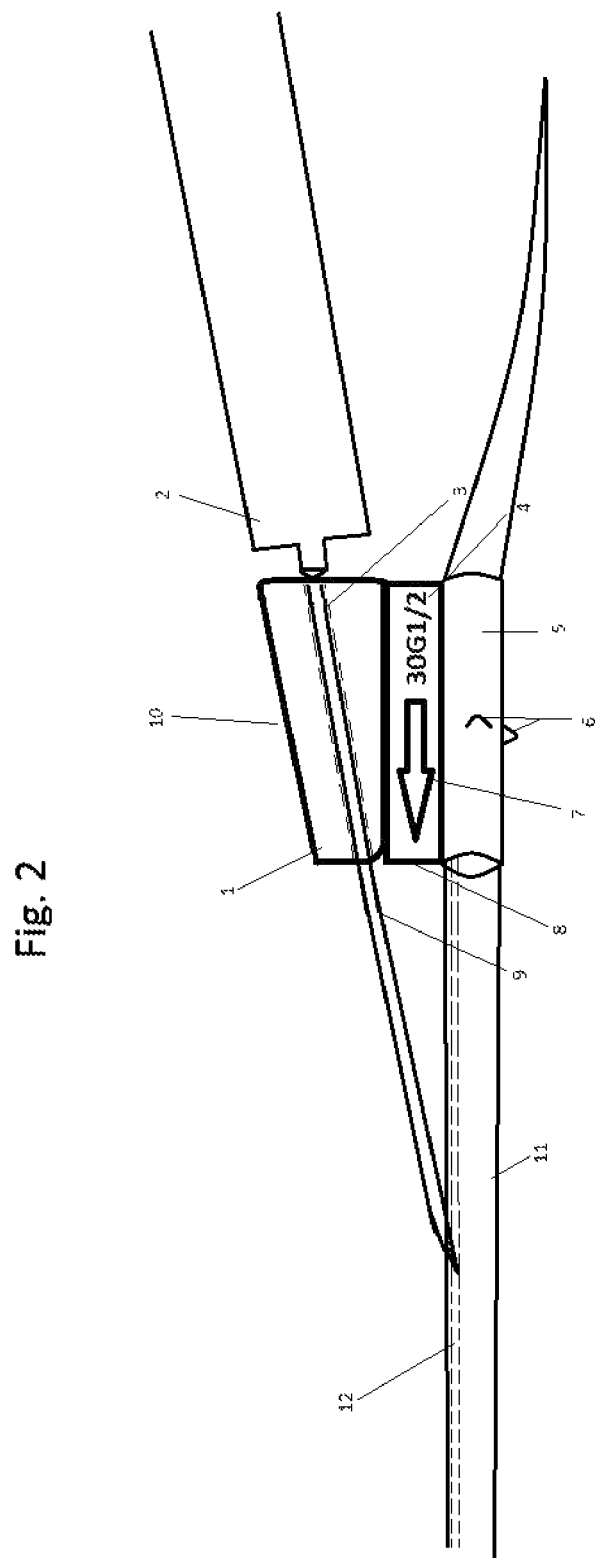
FIG. 2 depicts a mouse tail and the invention placed on the tail. The figure depicts the appropriate positioning of the clip on the tail of the mouse for accurate injections. A needle inserted into the invention and puncturing the tail vein is also depicted.
Figure 3:
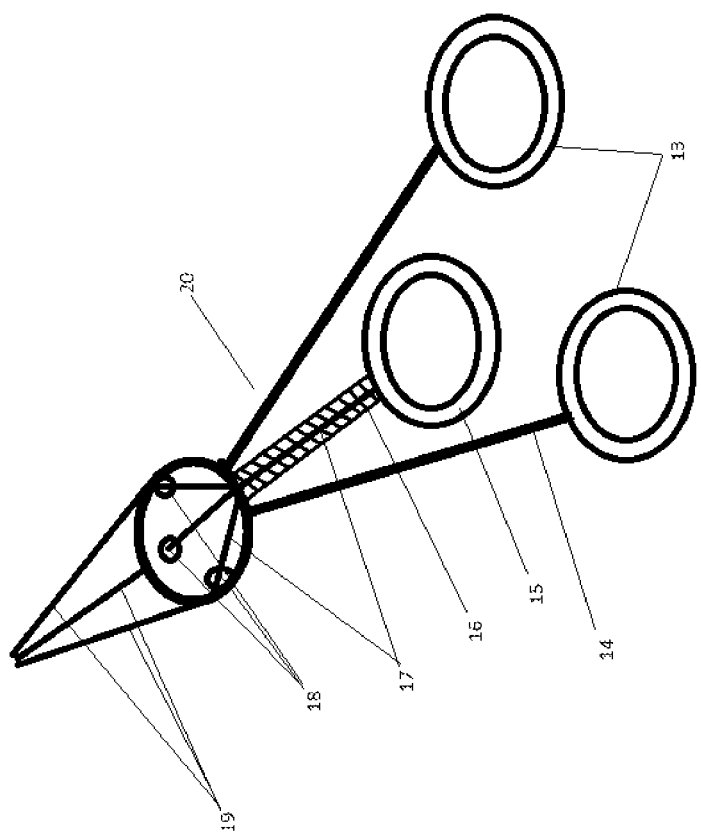
FIG. 3 depicts the placement tool, whose hands are meant to insert into the retainer holes on the tourniquet to expand it.

The following is a detailed description of the invention to allow those skilled in manufacturing such products to understand and create the invention, and include any variations apparent to them that fall within the scope of the present invention.

The clip 10 consists of an elastic material which acts as a tourniquet 5, and a rigid plastic ring 1 attached above the tourniquet 5. The tourniquet 5, when not stretched, should have an inner diameter of no larger than 2.5 mm and no less than 2 mm, and has an inner diameter of no larger than 5 mm when stretched. The tourniquet 5 material should be elastic to accommodate these diameters, but also maintain low pressure to prevent complete vessel occlusion and mouse death.

The plastic ring 1 should be rigid and attached to the outer portion of the tourniquet 5 via a support platform 8. The attachment can be accomplished using water-proof adhesive or plastic spot welding. The ring 1 will be made to an inner diameter 3 equivalent to the needle's 9 outer diameter. The ring 1 will be made such that the top portion is beveled, and the needle 9 will traverse at an angle when inserted into the ring 1. Additionally, the needle 9 will only be allowed to traverse up to a certain length to allow the needle bore to penetrate the vessel 12. This will be accomplished by making the width of the ring 1 wider so the ring's wall prevents further movement of the needle 9 when it touches the needle's plastic retainer 2. The thin support platform 8 made of the same material is added underneath the ring 1 and attaches to the tourniquet 5.

Each ring 1 size will be made to fit a standard needle 9 gauge and length, which will be marked 4 on the support platform 8. The ring's 1 width will also need to be made to accommodate for the length of the needle 9, in order to prevent further movement into the vessel 12. This also allows the researcher to attain leverage when depressing the plunger to inject the compound. A tool 20 can also be utilized to place the tourniquet 5, where the researcher inserts the tool's hands 19 into the plastic retainer holes 6 attached to the tourniquet 5, and then expands the hands 19 to a desired diameter, thereby expanding the tourniquet 5. The user can then simply insert the tail 11 within the tourniquet 5, and carefully release the tourniquet 5 onto the tail 11 at the desired position.

To use the clip 10, the researcher will expand the tourniquet 5 by hand, or using the tool 20, and place the tourniquet 5 at the desired position on the tail 11. The placement tool 20 has two holes 13 for the thumb and medial finger, with a central hole 15 for the index finger. The central hole 15 is attached to a metal wire 17 surrounded by a spring 16. The wire 17 is subsequently and individually attached to the joint 18 of each hand 19. When the user pulls the central hole 15, the wire 17 pulls on each hand 19 to rotate around their respective joints 18 and separate. The user will determine how far the hands 19 should separate to insert them into the retainer holes 6 of the tourniquet 5. Once the tourniquet 5 is in the desired position, the researcher adjusts the tourniquet 5 so the ring's alignment arrow 7 lies above the vessel 12 of choice, and then releases the tourniquet 5 by releasing the central hole 15 and allowing the hands 19 to revert back to their closed position. The researcher will then insert the appropriate needle 9 with syringe 2 into the ring's orifice 3. After the needle 9 enters the ring 1, the point of the needle punctures the vessel 12, and further travel of the needle 9 into the ring 1 stops due to the width of the ring 1 preventing further movement. Once the researcher has confirmed that the needle 9 has entered the vessel 12, then a slight nudge forward by pushing the needle 9 along with the ring 1 will allow the bore of the needle 9 to enter the vessel 12, and the researcher will inject the compound by depressing the plunger and using the ring 1 for leverage. Afterwards, the user removes the needle 9 and immediately removes the tourniquet 5 by sliding it down the length of the tail, or using the tool's hands 19 to remove the tourniquet by reversing the procedure used to place the tourniquet 5 on the tail 11.

The clip 10 is distinguished from previous inventions by offering a low-cost, sterile, user-friendly, and more accurate alternative to the automated tail vein injection system and an experienced researcher.

REFERENCES CITED

| | | | |
|---|---|---|---|
| US2014023605 A1 | August 2014 | Chang et al. | 14/347,207 |

OTHER PUBLICATIONS CITED

Minasian, "A simple tourniquet to aid mouse tail venipuncture" Laboratory Animals, July 1980, 14(3): 205

The invention claimed is:

1. A system for the purpose of reducing variability in tail vessel injections performed in a laboratory setting comprising: a mouse tail vessel injection clip and a placement tool with a plurality of hands, wherein the mouse tail vessel injection clip comprises: a tourniquet, a ring, a platform with indicator markings, and retainer holes.

2. The system of claim 1, wherein the tourniquet, for use in wrapping around a tail of a mouse to constrict a tail vessel of a mouse, is made of an elastic material, and is attached to an underside of the platform.

3. The system of claim 1, wherein the ring, for use in accepting a needle to allow an accurate injection into a tail vessel of a mouse, is made of a rigid and plastic material, having an inner hole with a diameter and width ranging from 0.36 to 0.18 mm and 5 to 20 mm, respectively, is beveled at an angle ranging from 5 degrees to 45 degrees, and is attached to a topside of the platform.

4. The system of claim 1, wherein the retainer holes, each having an inner diameter ranging from 3 mm to 6 mm and for use in accepting the hands of the placement tool, is made of a rigid and plastic material, and is attached to an outer portion of the tourniquet on three sites.

5. The system of claim 1, wherein the plurality of hands of the placement tool consists of 3 hands, such that the placement tool is configured for inserting the 3 hands into the retainer holes to stretch open the tourniquet, is made of a rigid and plastic or metal material, has finger holes and 3 handles extending into the 3 hands, and has a metal wire connecting the 3 hands to the 3 handles.

6. The system of claim 1, wherein the platform is made of a rigid and flat material, with indicator markings depicting a needle gauge and direction to be used within the ring, and is attached to an underside of the ring and a topside of the tourniquet.

* * * * *